United States Patent
Lemke et al.

(10) Patent No.: US 9,878,085 B2
(45) Date of Patent: Jan. 30, 2018

(54) METHOD FOR THE ELIMINATION OF LEUKOCYTES FROM BLOOD

(71) Applicant: 3M INNOVATIVE PROPERTIES COMPANY, St. Paul, MN (US)

(72) Inventors: Horst-Dieter Lemke, Obernburg (DE); Frank Wiese, Wuppertal (DE); Bodo von Harten, Wuppertal (DE); Martin Konig, Dusseldorf (DE); Wolfgang Ramlow, Rostock (DE)

(73) Assignee: 3M Innovative Properties Company, St. Paul, MN (US)

( * ) Notice: Subject to any disclaimer, the term of this patent is extended or adjusted under 35 U.S.C. 154(b) by 469 days.

(21) Appl. No.: 13/794,910

(22) Filed: Mar. 12, 2013

(65) Prior Publication Data

US 2014/0008288 A1    Jan. 9, 2014

Related U.S. Application Data

(62) Division of application No. 12/065,628, filed as application No. PCT/EP2006/008585 on Sep. 2, 2006, now Pat. No. 8,501,008.

(30) Foreign Application Priority Data

Sep. 9, 2005  (DE) .................. 10 2005 043 237
Aug. 22, 2006 (DE) .................. 10 2006 039 197

(51) Int. Cl.
    *A61M 1/36*    (2006.01)
(52) U.S. Cl.
    CPC ... *A61M 1/3633* (2013.01); *A61M 2202/0439* (2013.01)

(58) Field of Classification Search
    USPC .... 210/645, 651, 491, 646, 650, 321.8, 800, 210/446; 264/41; 428/398
    See application file for complete search history.

(56) References Cited

U.S. PATENT DOCUMENTS 4,125,468 A * 11/1978 Joh et al. ............... 210/321.8
4,252,653 A *  2/1981 Beck .................... B01D 15/08
                                                  210/321.87

(Continued)

FOREIGN PATENT DOCUMENTS

EP    0312595 A1   4/1989
EP    0371189 A2   6/1990

(Continued)

*Primary Examiner* — Dirk Bass
(74) *Attorney, Agent, or Firm* — Scott A. Baum

(57) ABSTRACT

The invention relates to a method for reducing the number of leukocytes in blood through treating the blood in an arrangement of a plurality of fibers based on organic polymers, whereby the blood is channeled along the fibers and whereby the reduction in leukocytes from the blood occurs essentially through adsorption on the fibers, characterized in that the plurality of fibers based on organic polymers is fixed in a housing with an inlet arrangement and an outlet arrangement, and that the blood is channeled via the inlet arrangement into the housing, flows through the housing with the plurality of fibers made from organic polymers, and exits the housing via the outlet arrangement, that the arrangement of the fibers shows a high degree of order, that the blood flows along the external surface of the fibers, and that the fibers cause a generation of the complement activation product C5a in a concentration of at least 10 μg per m² of fiber surface.

13 Claims, 9 Drawing Sheets

(56) References Cited

U.S. PATENT DOCUMENTS

| | | | |
|---|---|---|---|
| 4,424,132 A | | 1/1984 | Iriguchi |
| 4,497,104 A | * | 2/1985 | Fowles et al. ............... 29/419.1 |
| 4,882,106 A | * | 11/1989 | Johnson et al. ............... 264/41 |
| 4,882,223 A | | 11/1989 | Aptel et al. |
| 4,925,572 A | | 5/1990 | Pall |
| 5,407,581 A | * | 4/1995 | Onodera et al. ............. 210/654 |
| 6,045,701 A | | 4/2000 | Ung-Chhun et al. |
| 6,193,896 B1 | | 2/2001 | Kim et al. |
| 6,375,876 B1 | | 4/2002 | Kessler et al. |
| 6,498,007 B1 | | 12/2002 | Adachi et al. |

FOREIGN PATENT DOCUMENTS

| | | |
|---|---|---|
| EP | 0285812 A1 | 9/1996 |
| EP | 0732141 A1 | 9/1996 |
| EP | 0732142 A2 | 9/1996 |
| EP | 1230940 A1 | 8/2002 |
| WO | WO 95/18665 A1 | 7/1995 |

\* cited by examiner

METHOD FOR THE ELIMINATION OF LEUKOCYTES FROM BLOOD

This application is a divisional application claiming the benefit of co-pending application Ser. No. 12/065,628 filed Apr. 14, 2008.

The invention relates to a method for the removal of leukocytes from blood as well as a device for executing this method.

Blood essentially consists of plasma and cellular elements. These include erythrocytes (red blood cells), thrombocytes (platelets) and leukocytes (white blood cells). White blood cells include lymphocytes, monocytes and neutrophil granulocytes (neutrophils, PMN). Lymphocytes play a decisive role in specific immunity; monocytes and neutrophil granulocytes are cell types that are involved in non-specific immune system defense or reaction to inflammation. Their task is, e.g., to destroy invading microorganisms that have previously been identified as foreign by certain endogenous proteins (i.e., by C3b of the complement system or by immunoglobulin G, IgG).

If the cells have approached the microorganisms, they release oxygen radicals as well as proteases, by which means the microorganisms are killed in order to be phagocytized later. If this reaction is incompletely executed, or if it runs out of control and becomes chronic, the body's own tissue can be damaged by the release of aggressive oxygen radicals and proteases. During an inflammation, an intensive communication and coordination using, among others, various cytokines, occurs between all cell types. The reaction is very complex and has not been completely elucidated. However, it leads ultimately to the clinically observed inflammatory symptoms of swelling, redness and fever. An increase in, among others, certain messengers and in monocytes and neutrophil granulocytes, which are produced in the bone marrow and circulate in the blood, is typical. In addition to the pro-inflammatory cytokines mentioned above, the complement components C3a and C5a are produced by activation of the proteins C3 and C5, and serve as a degree of complement activation during the inflammatory or acute-phase reaction.

Currently, extracorporeal therapies are used for a series of inflammatory diseases, i.e. for colitis ulcerosa, Crohn's disease and rheumatoid arthritis. According to the prior art, a certain number of cells (presumably especially monocytes and neutrophil granulocytes) are removed from the patient by recirculating the patient's blood extracorporeally and treating it with a cell filter. For example, columns filled with particles or beads of cellulose acetate are used as leukocyte filters. In this case, the removal occurs primarily via cell adsorption of cells on the surface of the beads. Such products are already commercially available. In this case, blood is conducted through a column that contains cellulose acetate beads. The cellulose acetate beads particularly reduce granulocytes and monocytes contained in the blood via adsorption.

U.S. Pat. No. 6,498,007 discloses a method for removal of leukocytes from blood via adsorption onto a carrier. In the process, blood is brought into contact with this carrier, preferably in the form of the so-called beads, whereby the carrier shows a higher affinity to infected, activated or defective leukocytes than to uninfected, non-activated or non-defective leukocytes.

Alternatively, non-woven or woven fabrics are used for extracorporeal removal in the leukocyte filter. For example, products based on non-woven fabrics are used for the removal of leukocytes from conserved blood components for transfusion (e.g. an erythrocyte or platelet concentrate), in which products the cell removal occurs primarily via mechanical filtration by means of the non-woven fabric. Typically, for transfusions, 500 ml batches of blood are filtered in less than one-half hour. The process is gravity driven and takes place in a single pass and not in circulation. In order that a cell filter may be employed in extracorporeal circulation, approximately 1-6 l of pump-driven blood would have to be filterable for several hours. Polypropylene non-woven fabric in a cylindrical housing with a supply connection at the front end and a discharge connection at the opposite end are commercially available for this. By means of the non-woven fabric used, leukocytes are retained due to filtration and adsorption effects.

According to EP 1 230 940 as well, a filter for the removal of leukocytes from blood is used. The filter can be a non-woven fabric, a woven fabric, or a porous flat or hollow-fiber membrane. The blood to be treated flows through the non-woven fabric, woven fabric or the porous membrane. The filter material has a coating made of a hydrophilic, synthetic polymer. This coating allows the passage of thrombocytes through the filter with simultaneous removal of leukocytes via adsorption.

WO 95/18665 discloses a filter and a method for removing leukocytes and virus-inactivating substances from plasma or other blood fractions. The filter is based on a net made of textile fibers. Ligands with a high affinity to virus-inactivating substances or leukocytes are covalently bonded to the net. This concerns a selective, yet technically very complex method, because the ligands have to be connected directly or via linkers to a polymer matrix.

The residence of the leukocytes by such filters is based on cell trapping in the non-woven fabric as well as a more or less strong adsorption of the cells on the fiber surface. However, in this method the various blood cells are subjected to high mechanical stresses, which can lead to a cell activation or even to destruction of the blood cells.

An essential disadvantage of the existing systems and methods consists in that the various cell types cannot be targeted or specifically adsorbed, and that lymphocytes, thrombocytes and erythrocytes are adsorbed along with the monocytes and granulocytes. This can be, according to the indications in each case, either unnecessary, or even harmful to the patient. The adsorption of thrombocytes presents a special case. Following activation, thrombocytes play a central role in blood coagulation. This must be counteracted medicinally, such as by means of the administration of heparin as an anticoagulant, so that blood clotting does not occur during the extracorporeal circulation. Blood coagulation that occurs despite the anticoagulant leads to a clogged filter.

A further disadvantage of conventional leukocyte filters is that they are often quite difficult to set up prior to clinical use, e.g., in relation to deaeration. Air bubbles in an extracorporeal circulation potentially represent a danger to the patient and are thus highly undesirable. Setup of the filter becomes better and its use becomes safer to the same degree that the possibility of removing air present in the filter becomes simpler.

It is therefore the object of the present invention to make a method for the reduction in leukocytes from blood available, in which the disadvantages of the prior art are at least minimized, in which the blood is treated gently and which allows alternatives in order to remove various cell types in a targeted manner. It is the further object of the present invention to make available a device for executing such a method.

This object is achieved by a method for reducing the number of leukocytes in blood through treating the blood in an arrangement of a plurality of fibers based on organic polymers, whereby the plurality of fibers is fixed in a housing with an inlet arrangement and an outlet arrangement, the blood is channeled via the inlet arrangement into the housing, then flows through the housing, whereby the blood flows around the fibers on their external surface, and finally exits the housing via the outlet arrangement, characterized in that fibers are used that cause a generation of the complement activation product C5a in a concentration of at least 10 μg per m² of fiber surface when blood circulates around their external surface, and that the arrangement of the fibers shows a high degree of order.

The invention also comprises a device for reducing the number of leukocytes in blood comprising a plurality of fibers based on organic polymers in a housing with an inlet arrangement and an outlet arrangement, characterized in that the arrangement of the fibers shows a high degree of order and that the fibers based on organic polymers cause a generation of the complement activation product C5a in a concentration of at least 10 μg per m² of fiber surface C5a is a cleavage product of the plasma protein C5. The maximum value of the C5a concentration in blood is therefore limited by the concentration of C5 in the blood plasma, whereby the C5 concentration in the plasma is subject to large individual fluctuations and can be from approximately 40 mg/l to 150 mg/l. Based on the molar mass ratio of C5 to C5a, this results therefore in a theoretical maximum concentration of 9 mg/l C5a in the blood.

The concentration of the complement activation product C5a in blood plasma is determined by using a sandwich ELISA (Enzyme Linked Immunosorbent Assay) produced by DRG Diagnostics in Marburg, Germany. After contact by the fibers with human donor blood (5 U/ml heparin), 1.8 ml of blood is removed at various times and is stopped with 0.2 ml of a 100 mM EDTA solution. Prior to the analysis, in accordance with the manufacturer's instructions, the C5 was precipitated (200 μl plasma+200 μl precipitate reagent). 50 μl of supernatant was used in the determination. The detection sensitivity of the assay lies at <0.02 μg/l, the recovery rate of C5a in the plasma at 86-114% and the coefficient of variation at 5-8% (intra-assay) and 6-10% (inter-assay). The C5a concentration measured is dependent on the blood volume and the fiber surface. Therefore, for the determination of the C5a concentration in relation to the external surface of the fibers, the absolute C5a content in the sample must be determined and placed in relation to the external fiber surface. Therefore, a ratio of blood volume (V) to fiber surface area (A), V/A, of 0.3 L/m² is to be maintained. The determination of the area-related C5a concentration occurs after a treatment period of 3 hours, that is, the blood sample is channeled for 3 hours along the external surface of the fibers, during which a linear flow rate of 5 to 30 cm/min must be maintained. Because the test results are subject to donor-dependent, individual fluctuations, the number of samples N should amount to at least 2, and the average values of the samples should be stated.

Without wishing to be bound by the theory, it is suspected that an important relevance is accorded to complement activation in the treatment of inflammatory diseases, and that a reduction in the number of leukocytes in combination with a complement activation is significantly more effective than a reduction in the number of leukocytes alone. For this to occur, the complement activation, determined by the concentration of C5a in the blood, must lie above the threshold value according to the invention.

A connection between the parameters leukocyte count and C5a is probably due to the fact that certain leukocytes can be activated by C5a. The activation by C5a and other factors has the effect that the cells become more adhesive (stickier) and therefore bonding to C5a generating surfaces is enhanced.

It is therefore preferred that the fibers cause a further increased generation of the complement activation product C5a in a concentration of at least 75 μg per m² of fiber surface.

It is especially preferred that the fibers cause a generation of the complement activation product C5a in a concentration of at least 100 μg per m² of fiber surface.

In order to avoid damage to the cells contained in the blood, it is important that the blood does not significantly penetrate the fiber material, and that it does not flow through the fiber material. Therefore a fiber material, or fibers, is preferred that has an impermeable surface, or in the case of a porous surface, that has a maximum pore size of 0.1 μm.

The fibers based on organic polymers can be multifilament fibers, i.e., fibers that consist of a plurality of individual filaments; preferably the fibers are monofilament fibers, i.e., they consist of one single filament.

Because the generation of the C5a required for the method of the invention is not only dependent on the polymer, but also on admixtures or on the degree of substitution of the polymer, the term 'based on organic polymers' comprises the polymer materials as such, substitutions and mixtures thereof, copolymers of these materials as well as any added auxiliary materials or additives, e.g., hydrophilizing agents.

In the sense of the present invention, a high degree of order is understood to mean that the fibers lie in a similar arrangement with respect to each other, or that a large proportion of the fibers are arranged next to each other along their extension direction. Theoretically, a bundle of straight fibers, which lie parallel to each other, has the highest degree of order. A bundle of corrugated or crimped fibers, in which the fibers in the fiber bundle all show the same extension direction, also has a high degree of order in the sense of the present invention. In the sense of the present invention, a fiber bundle that is laid in a loop also comprises a high degree of order. In this case, the arrangement of the fibers to each other is also similar. It is additionally understood that a high degree of order means that at least 30% of the fibers lie parallel. Furthermore, this includes fibers that exist in several layers, whereby the fibers are arranged essentially parallel to each other within each layer. The parallel fibers in one layer can, however, cross the parallel fibers in another layer. Arrangements of this type are described in EP 285 812. Non-woven fabrics or randomly-laid fiber mats, in which the fibers exist completely without order and mixed with each other, do not constitute the arrangement with a high degree of order according to the invention. In comparison with non-woven fabrics, the arrangement of the fibers with a high degree of order in accordance with the invention shows a greater surface area and, when used in the method of the invention, a uniform blood film thickness. The high degree of order ensures that the blood flowing past the fibers shows comparably low turbulence and the cells contained in the blood are exposed to a lower shear stress. Additionally, the high degree of order ensures that the formation of dead spaces and preferred channels, so called shunts, is largely prevented. By this means, a particularly gentle blood treatment is achieved.

The high degree of order also ensures that the reduction in the number of leukocytes is essentially not produced by a sieve effect, as this would be the case, e.g., with a non-woven fabric, but by adsorption effects, by which means an especially gentle blood treatment is made possible. Additionally, the sieve effect that appears in the case of a non-woven fabric also inevitably causes an undesired reduction in other cellular blood components, e.g., thrombocytes.

For the method of the invention and the device according to the invention, not only are solid fibers suitable, but hollow fibers can be also used. Hollow fibers have an internal and an external surface. The flow is along the external surface when hollow fibers are used, as is also the case for solid fibers. Prior to or after the flow of the blood around the external surfaces of the hollow fibers, the blood can be allowed to flow through their lumina. It has been demonstrated, however, that no advantage is achieved by the additional flow through the lumen. Needless to say, hollow fiber membranes with impermeable or porous structures can also be used as hollow fibers. Care must be taken thereby that the method of the invention is so executed, that the blood does not essentially penetrate the hollow fiber or the hollow fiber membrane and flow through the membrane wall.

The number of fibers lies preferably in the range from 2000 to 20,000 fibers, particularly preferably in the range from 4000 to 14,000 fibers. The external diameter of the fibers should lie between 0.05 mm and 2 mm, preferably between 0.1 mm and 2 mm, and particularly preferably between 0.2 mm and 1 mm.

Preferably the arrangement of the fibers has a specific surface area for blood treatment of between 0.1 and 100 cm$^2$ of fiber surface per ml of blood to be treated, preferably between 0.5 and 20 cm$^2$ of fiber surface per ml of blood to be treated. The amount of the blood to be treated results from the duration of the blood treatment and the volumetric flow rate.

Fibers made from natural polymers or from polymers that were produced synthetically are considered to be fibers made from organic polymers. Fibers made from natural polymers are particularly those based on cellulosic polymers, which also comprises fibers that are subject to the so-called polymer-analog reaction. Examples of such fibers based on cellulose are those made from regenerated cellulose, cellulose acetate, or modified cellulose, such as, e.g., cellulose ester, cellulose ether, cellulose modified with benzyl groups (benzyl cellulose) or cellulose modified with diethylaminoethyl or mixtures of these cellulosic polymers. In the method of the invention, a large reduction in the number of leukocytes is achieved with fibers based on cellulosic polymers; a particularly large reduction is obtained with fibers made of regenerated cellulose. Furthermore, fibers based on chitin or chitosan can be used.

Under organic polymers, such polymers that are produced using synthetic means are also understood. Fibers made of synthetic polymers of the following type can be used: those that consist of polyolefins, polyamides, polyacrylonitrile, polycarbonates or polyesters as well as modifications, blends, mixtures or copolymers of these polymers. Preferably, those polymers are used that are based on sulfone polymers, such as polysulfone or polyether sulfone. These polymers can be admixed with additional polymers like polyethylene oxide, polyhydroxyether, polyethylene glycol, polyvinyl alcohol or polycaprolactone as additives. The fibers can have, in addition to this, a coating with an additive. The fibers preferably contain as well a hydrophilizing agent, e.g., polyvinylpyrrolidone, or a hydrophilic modification of this polymer.

The method is obviously suitable not only for the reduction in the number of leukocytes in whole blood, but also for the reduction in residual leukocytes in blood plasma or other blood concentrates. Therefore, within the context of the present invention, blood is understood to mean whole blood, blood plasma, or a blood concentrate.

It has been demonstrated that primarily leukocytes are reduced using the indicated fiber materials. In particular, the number of granulocytes and monocytes is primarily reduced using cellulosic fiber materials. Lymphocytes are only negligibly reduced with cellulosic materials.

It is therefore possible within the context of the method of the invention to reduce certain, targeted cell types from a class, such as the monocytes and granulocytes, but not the lymphocytes, from the class of leukocytes. Further, fiber materials based on cellulose distinguish themselves in that thrombocytes are only retained in low amounts.

In order to guarantee that all of the fibers come into contact with the blood flowing along the fibers in equal measure, the fibers can be arranged spaced apart from each other, for example using so-called spacer yarn. With regard to avoiding a sieve effect, a separation of the fibers is particularly advantageous. Spacer yarn of this type is particularly advantageous, because a uniform distance between the essentially parallel-lying fibers is guaranteed thereby. Arrangements with this type of spacer yarn are described for example in EP 732 141 or in EP 285 812. Preferably, the spacer yarn consists of the same material as the plurality of parallel threads. It is therefore also possible, by using a different fiber material for the spacer yarn, to reduce the number of additional cell types present in the blood.

In certain applications, it could be advantageous to additionally and selectively remove thrombocytes from the blood. For these applications, fibers made of polyethylene terephthalate (PET), polysulfone or polyether sulfone are suitable. Should a reduction in thrombocytes and leukocytes be desired, a combination of, for example, cellulosic fibers and PET fibers lends itself to the method of the invention.

As described above, the plurality of the fibers based on organic polymers is preferably located in a housing with an inlet arrangement and an outlet arrangement. For this, the fibers are usually embedded in a known manner with at least one of their two ends in a sealing compound bonded to the interior side of the housing, so that an outer space is formed around the fibers for the blood to flow through. For example, the ends of the fibers can be embedded in separate sealing compounds with the fibers extending essentially linearly between these sealing compounds. This type of construction is usually realized, for example, in conventional cross-flow mode driven hollow-fiber modules and appears, among other places, in commercially available dialysis modules. For modules of this type, when executing the method of the invention, blood flows through the outer space around the hollow fibers. The fibers can have only one end embedded in the sealing compound, or both ends can be embedded in the same sealing compound, and blood can flow around the other, free end that is not embedded, or around the loop formed, respectively. This type of fiber arrangement is described, for example, in EP 732 142 or in EP 371 189.

The filling ratio of the housing with the fibers made from organic polymers according to the invention should be between 10% and 70%, preferably between 30% and 60%. Because the fibers, depending on the fiber material, can swell strongly in varied levels due to contact with liquids, the determination of the filling ratio of the housing is to be established using fibers in their swollen state. Significant differences relating to fiber diameter in swollen and non-swollen states are observed in fibers that strongly swell, such as, for example, in those based on cellulose. Due to the swelling, various filling ratios therefore result when the fibers are present in their dry state. Fibers that do not, or do not appreciably swell, such as those made of polysulfone, show, in contrast, little or no difference in their swollen and not-swollen states for the determination of the filling ratio.

The filling ratio of the housing is to be limited to the given range, on the one hand to make a sufficiently large fiber surface available, on the other hand to avoid a sieve effect in the reduction in leukocytes in the method of the invention.

The residence time of the blood in the housing should be at least 0.5 min and should not exceed 5 min. During long residence times above 5 min, the blood's clotting tendency increases and, despite adding an anticoagulant, the risk of blood clots increases. During low residence times below 0.5 min, in contrast, the leukocyte adsorption is insufficient. Therefore a residence time of the blood in the housing of 1 to 3 min is preferred.

The linear flow rate of the blood through the housing with a plurality of fibers based on organic polymers should lie between 5 and 30 cm/min. The linear flow rate is understood to be the average rate at which the blood flows through the housing from the inlet arrangement to the outlet arrangement. In calculating the linear flow rate the so-called free cross-section of flow is used, which consists of the cross sectional area in the interior of the housing less the sum of the cross sectional areas of all fibers in the housing. Care should be taken hereby that, for the calculation of the cross sectional area of a fiber, the external diameter of the fiber is used, whereby for fiber materials that swell in contact with blood, the external diameter in its swollen state is relevant. Linear flow rates below 5 cm/min promote thrombocyte aggregation and blood clotting. Flow rates above 30 cm/min impede the adsorption of the cellular blood components on the fiber surface.

As has already been explicated, the fibers based on organic polymers show a high degree of order in their arrangement. In a preferred embodiment of the method of the invention or the device of the invention, the fibers based on organic polymers appear as a fiber bundle formed from essentially parallel fibers. In a further preferred embodiment of the method of the invention, the fibers based on organic polymers appear in one or more layers, whereby the fibers within each layer lie essentially parallel.

The invention will be explained in more detail on the basis of the following examples and figures; the area of the invention is, however, not limited by them.

EXAMPLE 1

Blood samples are treated with the method of the invention, using hollow fibers made from regenerated cellulose, and the number of leukocytes, the number of certain types of leukocytes, the number of thrombocytes as well as the generation of the complement activation product C5a is determined as a function of time.

Figure 1:
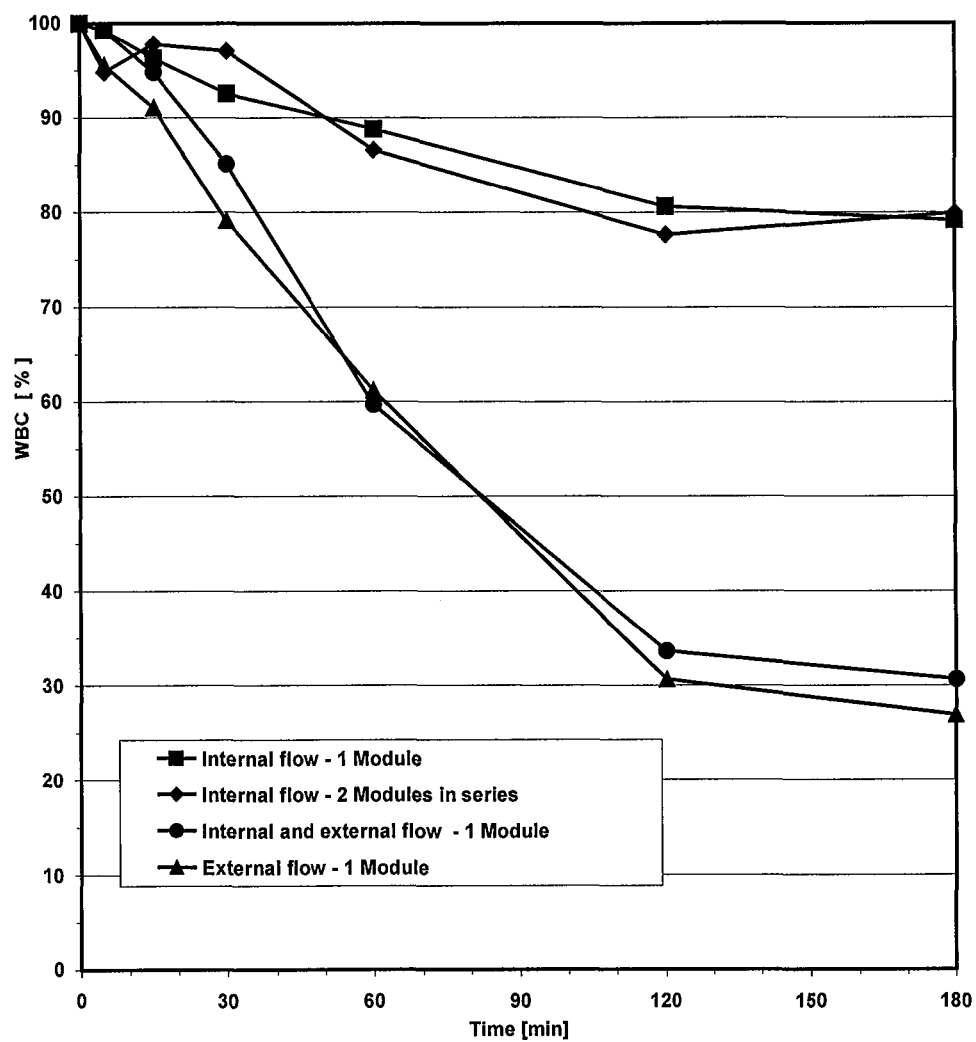
FIG. 1 shows the reduction in the number of leukocytes in a blood sample effected by the method of the invention, using hollow fibers made from regenerated cellulose, as a function of time.

FIG. 1 shows the relative percentual reduction in the number of leukocytes (WBC—white blood cells) in a blood sample treated with the method of the invention. For this purpose, a sheet of hollow fibers made of regenerated cellulose with an external surface area of 1.36 $m^2$ and an internal surface area of 1.27 $m^2$ was used. The hollow fiber sheet, consisting of 7400 fibers with a fiber diameter of 242 μm in the swollen state and a length of 260 mm, was arranged for this purpose in a cylindrical housing with an interior diameter of 33 mm. The filling ratio of the housing was ca. 40%. 410 mm of human blood was used as a blood sample, which was circulated for a period of at most 3 hours with a flow rate of 50 ml/min, which corresponds to a linear flow rate of 10 cm/min. The residence time of the blood in the housing was 2.5 min. The test results presented in FIG. 1 clearly show that a pronounced reduction in the number of leukocytes occurs when the blood flows along the external surface of the fibers. Flow along the internal surface leads to only a small reduction in the cell numbers of ca. 15% of the initial volume. Flow along the internal and external surfaces offers no advantages over flow solely along the external surface. Additionally, a flow along the internal surface through two modules in series does not lead to a leukocyte reduction in the amount that can be achieved by a flow along the external surface, even though the blood's contact area with the fiber material, 2.54 $m^2$, is significantly larger than by flow along the external surface (1.36 $m^2$). From FIG. 1 it is apparent that a reduction in the number of cells is only obtained when the blood flows along the external surface of the hollow fibers. Hollow fibers with flow along the internal surface show very little or no cell adhesion. This is also the case when flow along the internal surface is combined with flow along the external surface.

Figure 2:
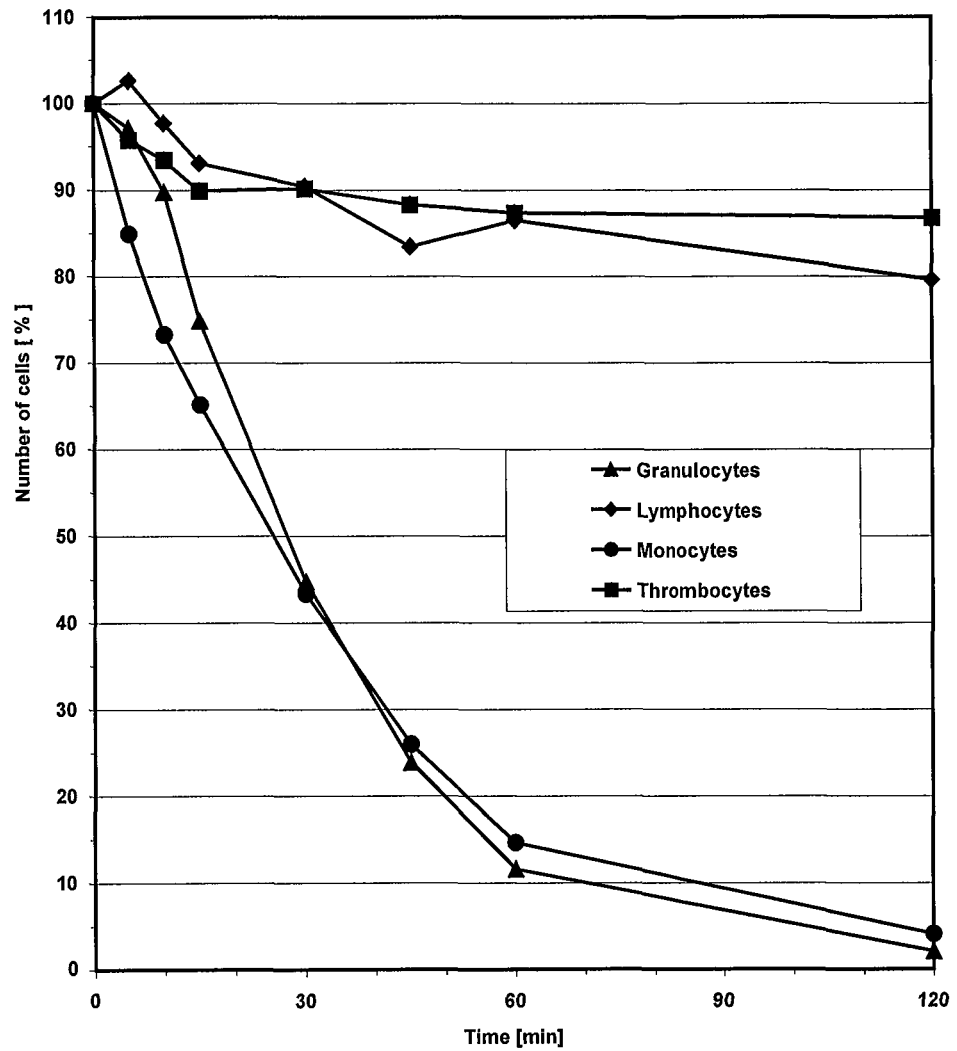
FIG. 2 shows the reduction in the number of granulocytes, lymphocytes, monocytes and thrombocytes in a blood sample treated with the method of the invention using hollow fibers made from regenerated cellulose, as a function of time.

FIG. 2 shows to what degree the number of individual types of leukocytes are reduced and what effect the method of the invention has on the number of thrombocytes. FIG. 2 shows the relative percentual reductions in the cellular number of monocytes, granulocytes, lymphocytes and thrombocytes in relation to the blood treatment time, which were determined using hollow fibers made of regenerated cellulose with an external surface area of 0.56 m² and 240 ml of human blood. 5400 fibers with a fiber diameter of 275 μm in the swollen state and a length of 120 mm were arranged for this purpose in a cylindrical housing with an internal diameter of 38 mm. The filling ratio of the housing was ca. 29%. The blood sample was circulated for a period of at most 3 hours with a volumetric flow rate of 117 ml/min, which corresponds to a linear flow rate of 14 cm/min. The residence time of the blood in the housing was 0.8 min. After a 3 hour period, monocytes and granulocytes were removed from the blood sample by over 95%; however lymphocytes and thrombocytes were reduced to a lesser extent, only ca. 20% and 15% respectively. By using regenerated cellulose, therefore, monocytes and granulocytes in particular can be removed from blood.

Figure 3:
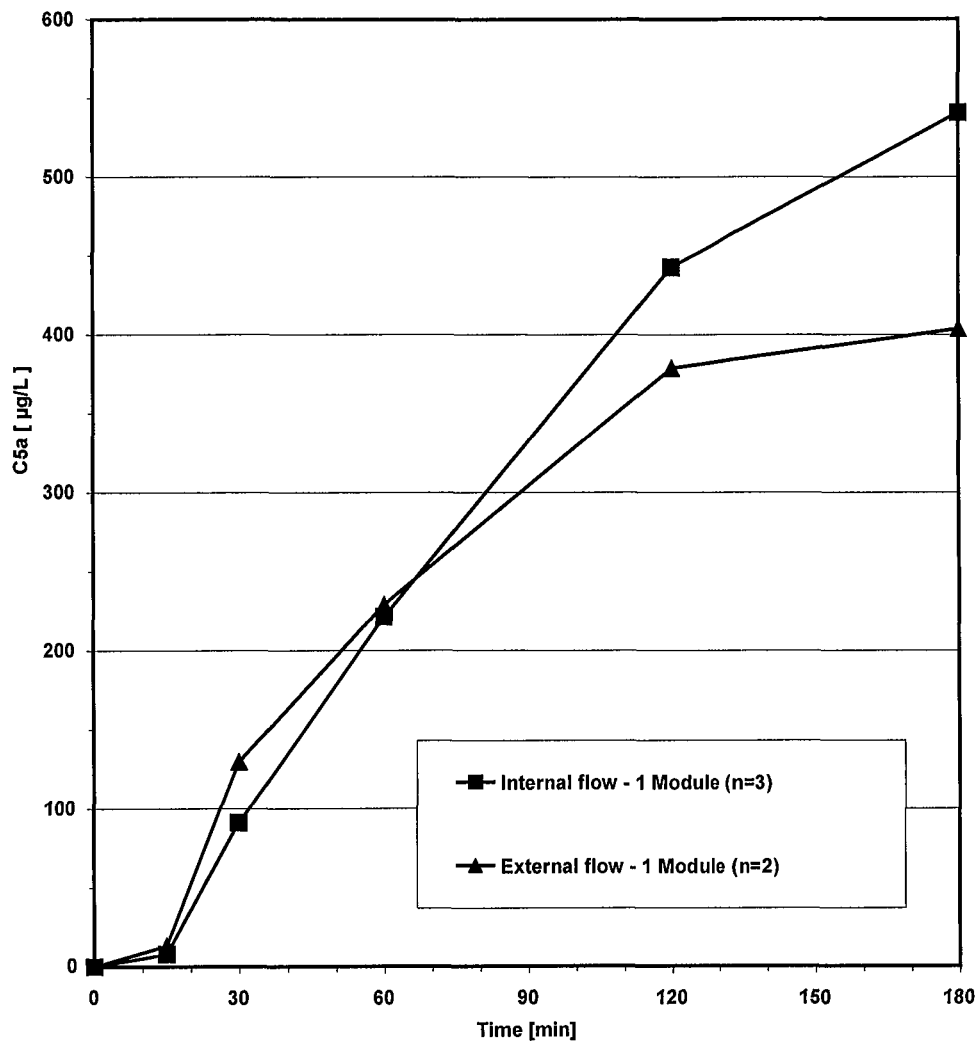
FIG. 3 shows the concentration of the complement activation product C5a in a blood sample treated with the method of the invention using hollow fibers made from regenerated cellulose, as a function of time.

FIG. 3 shows the concentration of the complement activation product C5a in a blood sample treated with the method of the invention. The tests were carried out under the same conditions as are presented under FIG. 1. Following a blood treatment of 3 hours, a C5a content of 403 μg/l was detected in the treated sample using flow along the external surface. This corresponds to a C5a generation of 165 μg in the treated blood sample, or 121 μg of C5a per m² of fiber surface.

EXAMPLE 2

Figure 4:
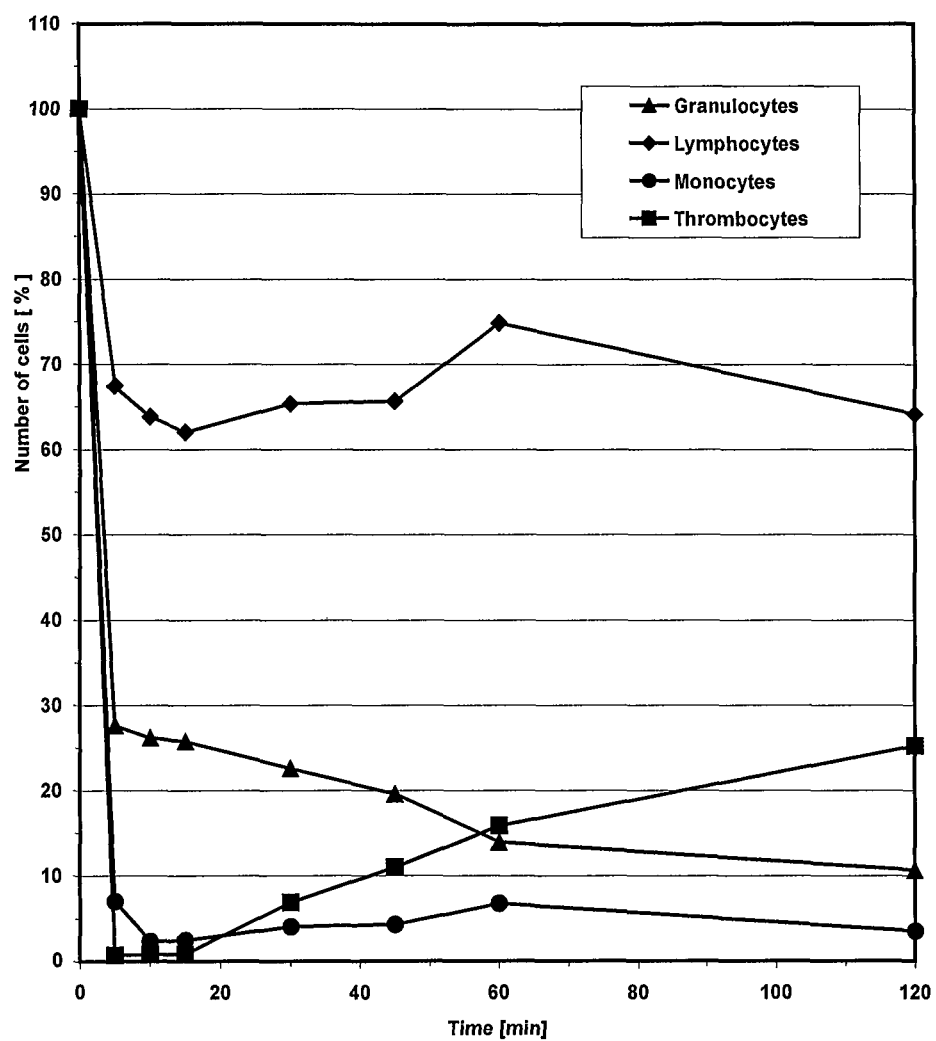
FIG. 4 shows the reduction in the number of granulocytes, lymphocytes, monocytes and thrombocytes in a blood sample treated with the method of the invention using hollow fibers made from regenerated cellulose and using additional PET fibers, as a function of time.

A hollow fiber module was used, as described in Example 1, FIG. 2, whereby however the hollow fiber bundle contained in addition polyethylene terephthalate (PET) fibers. FIG. 4 shows the time-dependent, relative percentual reduction in the cellular number of monocytes, granulocytes, lymphocytes and thrombocytes with the additional use of polyethylene terephthalate fibers. Otherwise, the test conditions correspond to the test conditions presented in Example 1 in relation to FIG. 2. A much faster removal of monocytes and granulocytes was achieved by the additional use of polyethylene terephthalate fibers in comparison to the exclusive use of fibers made of regenerated cellulose. After a mere 15 minutes, more than 95% of the monocytes and 75% of the granulocytes were removed from the sample. Approximately 60% of the lymphocytes and 75% of the thrombocytes were removed from the sample.

EXAMPLE 3

Figure 5:
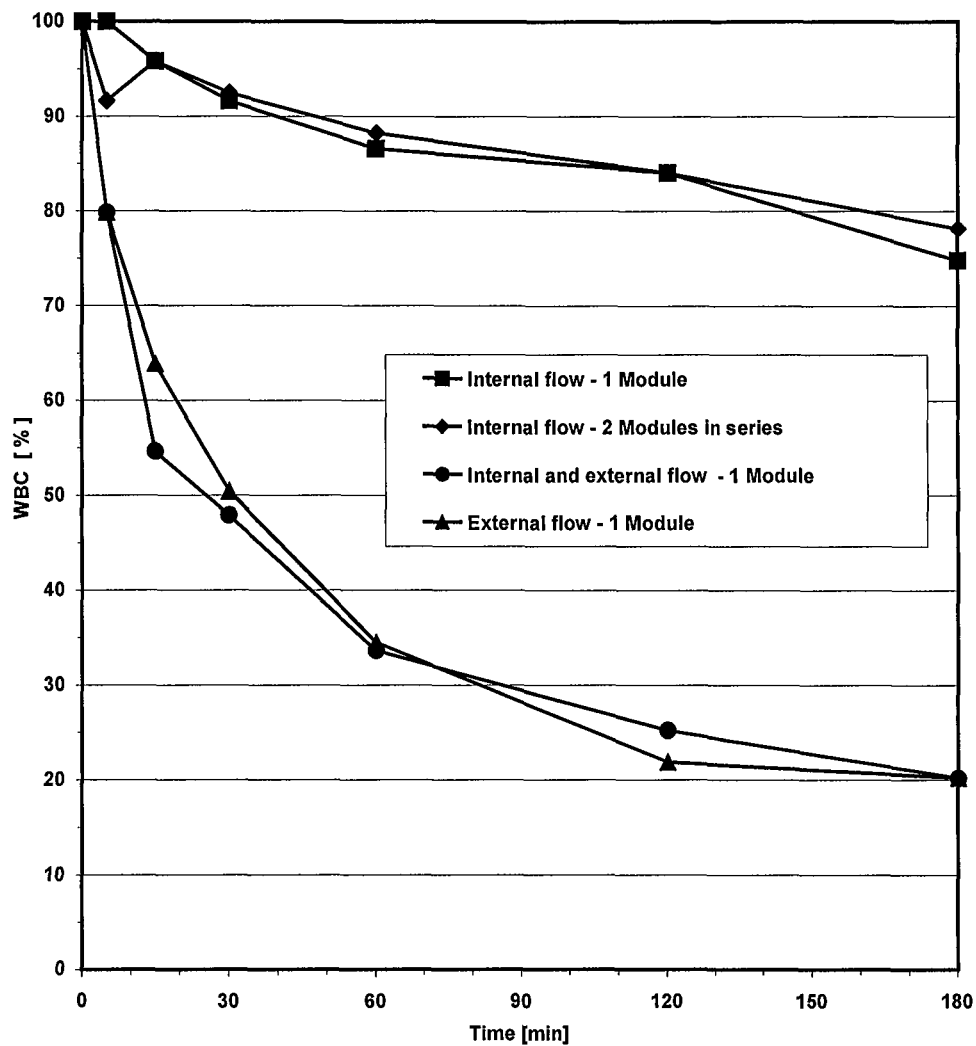
FIG. 5 shows the reduction in the number of leukocytes in a blood sample treated with the method of the invention using hollow fibers made from modified cellulose, as a function of time.

Blood samples were treated with the method of the invention using commercially available hollow fiber membranes made from cellulose modified with benzyl groups (benzyl cellulose) and the number of leukocytes as well as the generation of the complement activation product C5a were determined as a function of time. FIG. 5 shows the time-dependent, relative percentual reduction in the number of leukocytes (WBC—white blood cells) in relation to the initial volume in a blood sample treated with the method of the invention. In this case, hollow fibers were used with an internal surface area of 1.36 m² and an external surface area of 1.47 m². The blood sample treated was 440 ml of human blood. A multitude of 7900 fibers with a fiber diameter of 246 μm in the swollen state and a length of 240 mm were arranged for this purpose in a cylindrical housing with an internal diameter of 34 mm. The filling ratio of the housing was ca. 41%. The blood sample was circulated for a period of at most 3 hours with a volumetric flow rate of 50 ml/min, which corresponds to a linear flow rate of 9.4 cm/min. The residence time of the blood in the housing was 2.5 min. Analogous to the tests presented under FIG. 1, it becomes apparent that a pronounced reduction in leukocytes was achieved only when flow passed along the external surface. Although the internal surface is similar in size to the external surface, a flow along the internal surface leads only to a low reduction of ca. 15% of the initial number. Flow along the internal and external surfaces offers no advantages over flow along the external surface alone. Flow along the external surface parallel to the fibers effects a reduction in the leukocytes contained in the blood sample of 80%.

Figure 6:
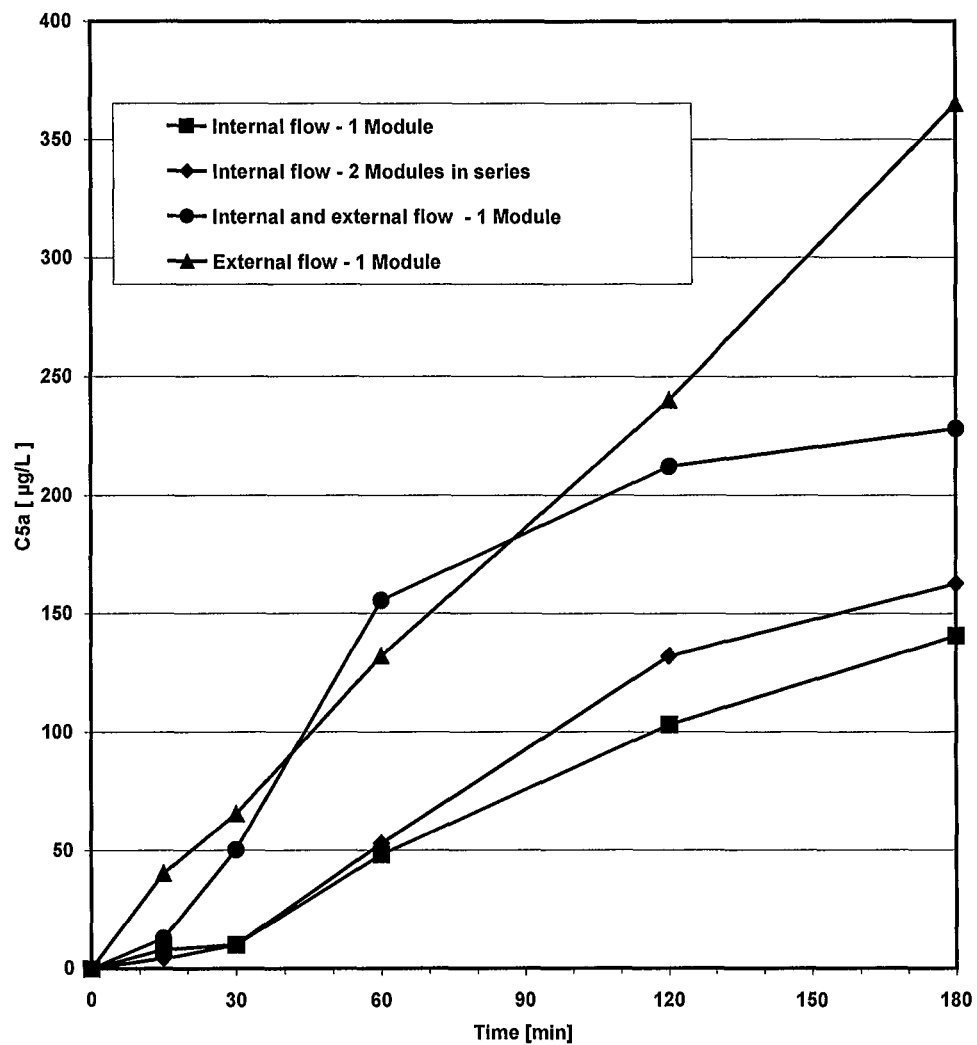
FIG. 6 shows the concentration of the complement activation product C5a in a blood sample treated with the method of the invention using hollow fibers made from modified cellulose, as a function of time.

The generation of the complement activation product C5a was examined under the same test conditions and with the same hollow fiber membrane presented under FIG. 5. The results are shown in FIG. 6. A clear distinction between flow along the internal and external surfaces, similar to FIG. 5, is also observed in this case. In spite of similarly sized contact surfaces, the C5a generation is ca. 2.5 times higher with flow along the external surface than with flow along the internal surface. After 3 hours of flow along the external surface, a C5a concentration of 365 μg/l was present in the blood sample. This corresponds to 161 μg in the blood sample or 109 μg of C5a per m² of fiber surface.

EXAMPLE 4

Figure 7:
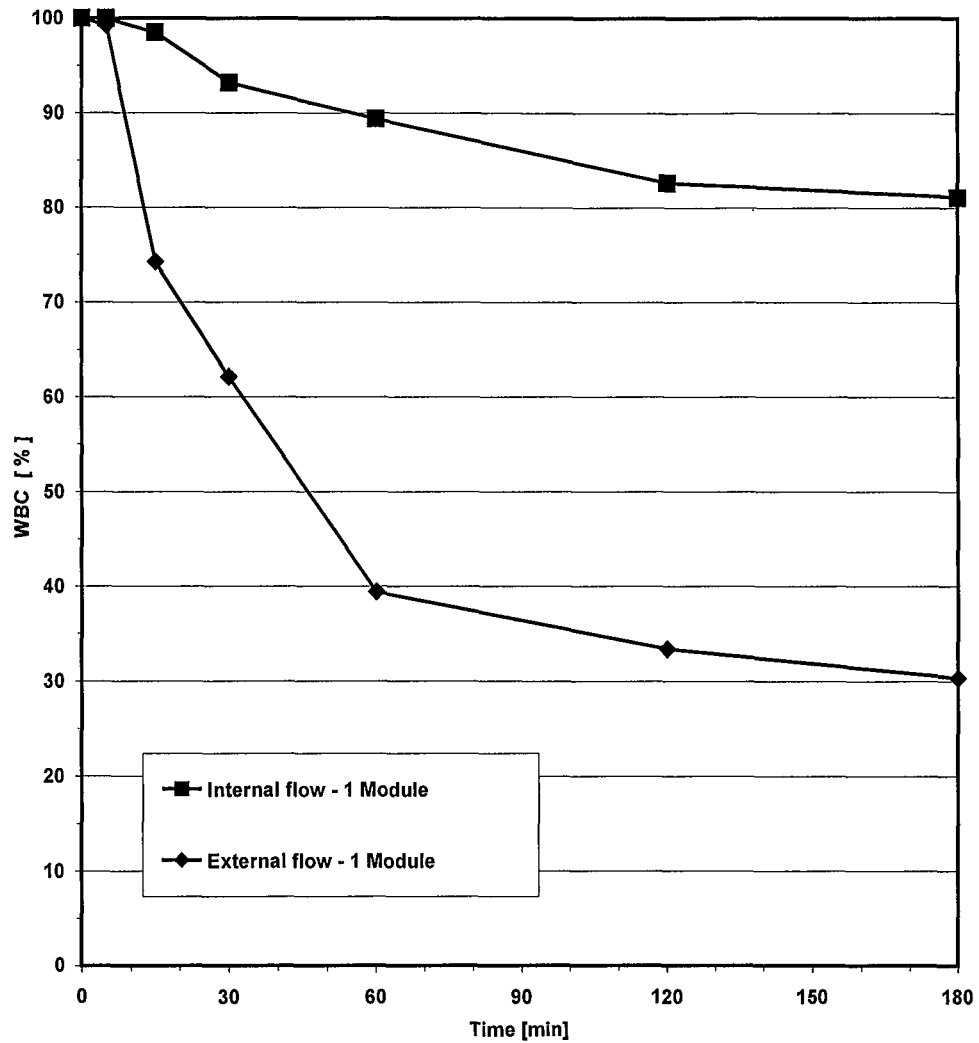
FIG. 7 shows the reduction in the number of leukocytes in a blood sample treated with the method of the invention using hollow fibers made from polyether sulfone, as a function of time.

A reduction in the leukocytes by using hollow fibers made from polyether sulfone is also possible, as is shown in FIG. 7. In this case, hollow fibers with an external diameter of 300 μm, an effective length of 275 mm, an internal surface area of 1.6 m² and an external surface area of 2.2 m² were used in a module with an interior diameter of 38.5 mm and loaded with 8500 fibers, i.e. with a filling ratio of ca. 52%. 381 ml of human blood was circulated through the module at a volumetric flow rate of 50 ml/min. The linear flow rate was ca. 9 cm/min, and the residence time was 3.1 min. It was shown here as well that hollow fibers made of polyether sulfone (PES) effect a reduction in the number of leukocytes by ca. 70% in flow along the external surface. Under the stipulated conditions for the determination of the C5a content in relation to the external fiber surface, an area-related C5a generation of 30 μg/m² was determined for the hollow fibers made from polyether sulfone.

EXAMPLE 5

Figure 8:
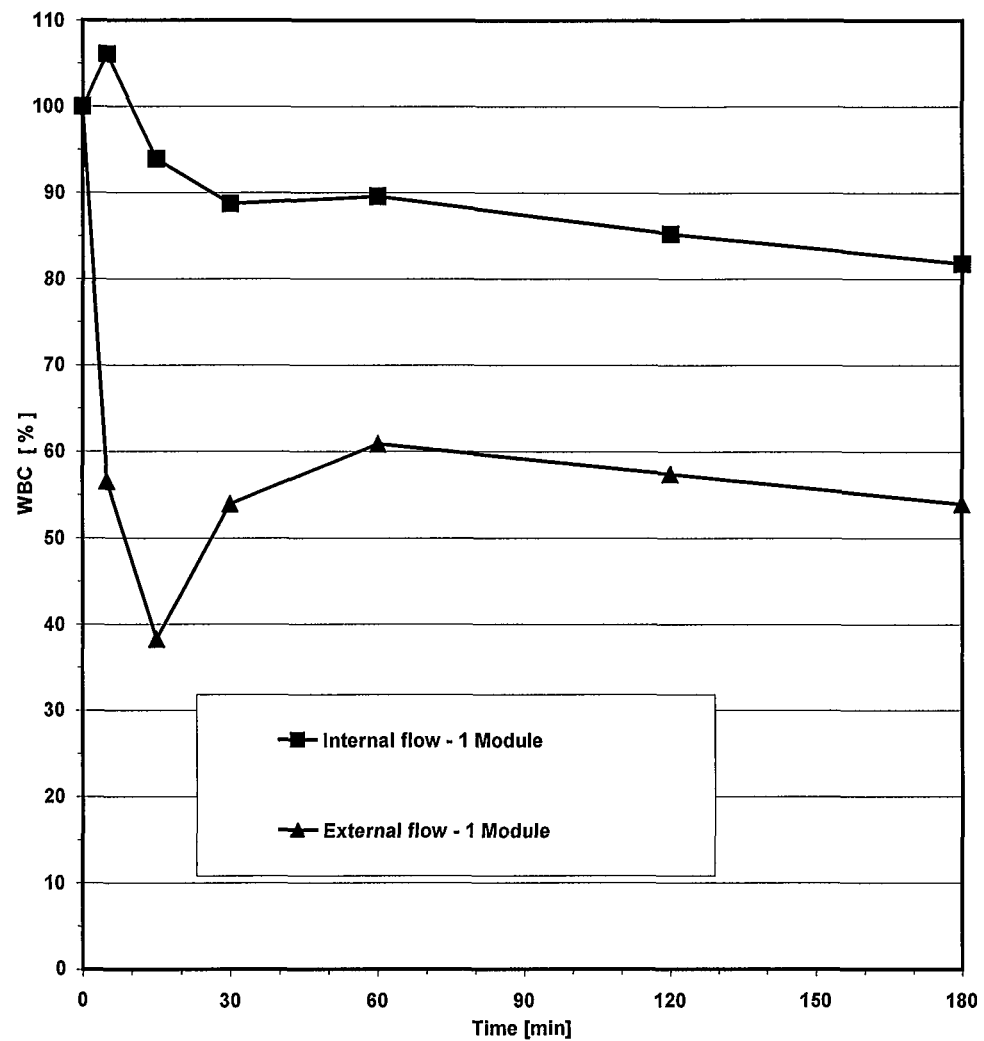
FIG. 8 shows the reduction in the number of leukocytes in a blood sample treated with the method of the invention using hollow fibers made from polyether sulfone and using additional PET fibers, as a function of time.

In Example 5, fibers made from PET were used in addition to hollow fibers made from polyether sulfone for the execution of the method of the invention. FIG. 8 shows the time-dependent, relative percentual reduction in the number of leukocytes (WBC—white blood cells) in a blood sample treated with the method of the invention. For this, hollow fibers made of polyether sulfone combined with fibers made from polyethylene terephthalate (PET) were used, with an internal surface area of 1.31 m² and an external surface area of 1.57 m². 8000 fibers with a fiber diameter of 260 μm and a length of 240 mm were arranged in a cylindrical housing with an interior diameter of 34 mm. The filling ratio of the housing was ca. 47%. 470 ml of human blood was used as a blood sample, which was circulated for a period having a maximum of 3 hours with a volumetric flow rate of 50 ml/min, which corresponds to a linear flow rate of 10 cm/min. The residence time of the blood in the housing was 2.3 min. It was shown here that hollow fibers made of polyether sulfone (PES) in combination with polyethylene terephthalate fibers effect a reduction in the number of leukocytes by ca. 50% with flow along the external surface. Flow along the internal surface leads to only a small reduction of ca. 18% of the initial volume.

Figure 9:
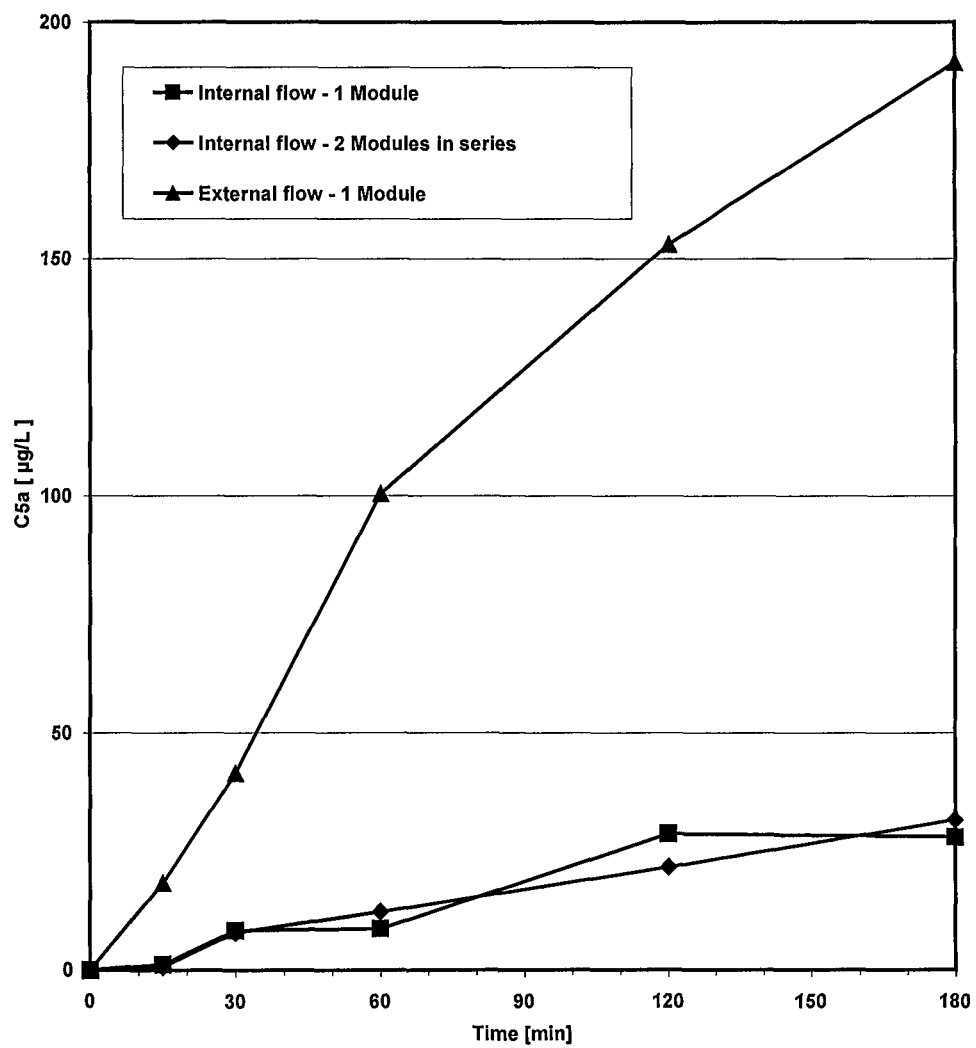
FIG. 9 shows the concentration of the complement activation product C5a in a blood sample treated with the method of the invention using hollow fibers made from polyether sulfone and using additional PET fibers, as a function of time.

Analogous to the results presented in FIG. 8, there is a large variation in C5a generation depending upon the flow. The results presented in FIG. 9 were determined using the same membrane as described in FIG. 8 and under the stipulated conditions for the determination of the C5a content in relation to the fiber surface. For flow along the internal surface, a C5a concentration of merely 30 µg/l was determined, while a C5a concentration of 192 µg/l was determined for flow along the external surface. The latter corresponds to a C5a generation of 90 µg in the treated blood sample, or 58 µg per m$^2$ of fiber surface.

The invention claimed is:

1. A device for reducing leukocytes in blood comprising a plurality of fibers based on organic polymers in a housing with an inlet arrangement and an outlet arrangement and wherein at least one of the ends of the fibers is embedded in a sealing compound bonded to an interior side of the housing forming an outer space such that the blood is channeled via the inlet arrangement into the outer space, then flows through the housing around an external surface of the fibers without flowing through the fiber material and exits the housing via the outlet arrangement, the fibers are solid fibers having an impermeable surface or a porous surface having a maximum pore size of 0.1 µm, the solid fibers are multifilaments or monofilaments, the fibers shows a high degree of order, and the fibers based on organic polymers generating a complement activation product C5a are in a concentration of at least 10 µg per m$^2$ on a fiber surface, whereby leukocytes are adsorbed onto the fiber surface.

2. The device according to claim 1 wherein the fibers generates the complement activation product C5a in a concentration of at least 75 µg per m$^2$ of fiber surface.

3. The device according to claim 1 wherein the number of the fibers based on organic polymers lies in the range of 2000 to 20,000 fibers.

4. The device according to claim 1 wherein a diameter of the fibers based on organic polymers lies between 0.05 mm and 2 mm.

5. The device according to claim 1 wherein a specific surface area of the arrangement of the fibers based on organic polymers lies between 0.1 and 100 cm$^2$ per ml of blood to be treated.

6. The device according to claim 1 wherein the fibers based on organic polymers consist of regenerated cellulose, cellulose acetate, or cellulose modified with benzyl groups (benzyl cellulose).

7. The device according to claim 1 wherein the fibers based on organic polymers consist essentially of polyether sulfone or polysulfone.

8. The device according to claim 1 wherein the plurality of fibers also contains fibers made of polyethylene terephthalate.

9. The device according to claim 1 wherein a filling ratio of the fibers in the housing lies in the range from 10% to 70%.

10. The device according to claim 1 wherein a residence time of the blood in the housing is from 0.5 min to 5 min.

11. The device according to claim 1 wherein a linear flow rate, at which the blood flows through the housing, is between 5 and 30 cm/min.

12. The device according to claim 1 wherein the fibers based on organic polymers are present as a fiber bundle with essentially parallel fibers.

13. The device according to claim 1 wherein the fibers based on organic polymers are present in one or more layers, and that the fibers within each layer lie essentially parallel.

* * * * *